United States Patent
Wortmann et al.

(10) Patent No.: US 10,730,827 B2
(45) Date of Patent: Aug. 4, 2020

(54) PROCESS FOR PURIFYING ALKANESULFONIC ANHYDRIDE AND PROCESS FOR PRODUCING ALKANESULFONIC ACID USING THE PURIFIED ALKANESULFONIC ANHYDRIDE

(71) Applicant: BASF SE, Ludwigshafen am Rhein (DE)

(72) Inventors: Juergen Wortmann, Ludwigshafen (DE); Jan Spielmann, Ludwigshafen (DE); Katharina Federsel, Ludwigshafen (DE); Feelly Ruether, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/605,973

(22) PCT Filed: Apr. 18, 2018

(86) PCT No.: PCT/EP2018/059864
§ 371 (c)(1),
(2) Date: Oct. 17, 2019

(87) PCT Pub. No.: WO2018/192954
PCT Pub. Date: Oct. 25, 2018

(65) Prior Publication Data
US 2020/0039927 A1 Feb. 6, 2020

(30) Foreign Application Priority Data
Apr. 18, 2017 (EP) .................................... 17166872

(51) Int. Cl.
*C07C 303/44* (2006.01)
*C07C 303/06* (2006.01)

(52) U.S. Cl.
CPC .......... *C07C 303/44* (2013.01); *C07C 303/06* (2013.01)

(58) Field of Classification Search
CPC .......................... C07C 303/44; C07C 303/06
See application file for complete search history.

(56) References Cited

U.S. PATENT DOCUMENTS

| | | |
|---|---|---|
| 4,035,242 A | 7/1977 | Brandt |
| 4,450,047 A | 5/1984 | Malzahn |
| 4,938,846 A | 7/1990 | Comstock et al. |
| 6,337,421 B1 | 1/2002 | Gancet |
| 2018/0319739 A1 | 11/2018 | Spielmann et al. |

FOREIGN PATENT DOCUMENTS

| | | |
|---|---|---|
| CN | 1810780 A | 8/2006 |
| DE | 197 43 901 C1 | 4/1999 |
| EP | 0 373 305 A1 | 6/1990 |
| EP | 0 505 692 A1 | 9/1992 |
| EP | 0 675 107 A1 | 10/1995 |
| GB | 977477 A | 12/1967 |
| GB | 1 350 328 A | 4/1974 |
| JP | 2003-238522 A | 8/2003 |
| WO | WO 00/31027 A1 | 6/2000 |
| WO | WO 2004/101860 A1 | 11/2004 |
| WO | WO 2005/069751 A2 | 8/2005 |
| WO | WO 2015/071365 A1 | 5/2015 |
| WO | WO 2015/086645 A1 | 6/2015 |
| WO | WO 2017/080991 A1 | 5/2017 |

OTHER PUBLICATIONS

Karger et al, Journal of Organic Chemistry, Mixed Sulfonic-Carboxylic Anhydrides. I. Synthesis and Thermal Stability, New Syntheses of Sulfonic Anhydrides, 1971, 36(4), pp. 528-531. (Year: 1971).*

International Search Report dated Jul. 13, 2018 in PCT/EP2018/059864, 4 pages.

Wynn, N.P. "Separate Organics by Melt Crystallization" Chemical Engineering Progress, American Institute of Chemical Engineers, vol. 88, No. 3. XP000246045, Mar. 1992, 10 pages.

Kapoor, R. et al. "Preparation, properties, and characterization of methanesulfonato complexes of arsenic(III), antimony(III), and bismuth(III)" Canadian Journal of Chemistry, vol. 65, No. 6, XP055489306, Jun. 1987, 6 pages.

Wei, D-W. et al. "Study on the synthesis and purification of methanesulfonic anhydride" Huaxue Fanying Gongcheng Yu Gongyi—Chemical Reaction Engineering and Technology, vol. 19, No. 1, 1 page (submitting English abstract only).

Craig, R.A. et al. "Cryoscopic Studies in Methanesulfonic Acid" Journal of the American Chemical Socety, vol. 72, 1950, 4 pages.

Berthoud, A. "Quelques propriétés physico-chlmiques des acides éthane- et méthane-sulfonlque" Helvetica Chimica Acta, vol. 12, 1929, 7 pages.

Sandemann, I. "The Methnesulphonic Acid-Sulphur Trioxide Complex: Detection by Raman Spectroscopy." Journal of the Chemical Society, 1953, pp. 1135-1138.

Robinson, E.A. et al. "The Reaction of Methanesulfonic Acid With Sulfur Trioxide" Canadian Journal of Chemistry, vol. 44, 1966, 9 pages.

* cited by examiner

*Primary Examiner* — Paul A Zucker (74) *Attorney, Agent, or Firm* — Oblon, McClelland, Maier & Neustadt, L.L.P.

(57) ABSTRACT

A process for purifying alkanesulfonic anhydride that includes feeding a stream containing alkanesulfonic anhydride, sulfuric acid, high boilers and residual low boilers into a melt crystallization to form crystals of the alkanesulfonic anhydride suspended in mother liquor, and solid-liquid separation to remove the crystals from the mother liquor.

20 Claims, 2 Drawing Sheets

PROCESS FOR PURIFYING ALKANESULFONIC ANHYDRIDE AND PROCESS FOR PRODUCING ALKANESULFONIC ACID USING THE PURIFIED ALKANESULFONIC ANHYDRIDE

The invention relates to a process for purifying alkanesulfonic anhydride. Alkanesulfonic anhydride for example can be used for producing alkanesulfonic acid. Thus, the invention further relates to a process for producing alkanesulfonic acid by using the alkanesulfonic anhydride.

Besides as raw material for the production of alkanesulfonic acid, alkanesulfonic anhydride also can be used together with alkanesulfonic acid as catalyst in alkylations, esterification reactions, polymerizations and the synthesis of heterocyclic compounds. The catalytic activity of alkanesulfonic acid is protected by alkanesulfonic anhydride which reacts with water and avoids the forming of catalytic less active alkanesulfonic acid hydrate.

Alkanesulfonic acids, in particular methanesulfonic acid (MSA), are employed in many applications either in pure form or as a mixture with water, other solvents or as a formulation with other active ingredients. The use of MSA is particularly widespread in electroplating, tinplate production and wire tinning. Alkanesulfonic acids are also employed as solvent or as catalyst in alkylation and esterification reactions for example. A further field of application for alkanesulfonic acids is the production of biodiesel where the typically employed sulfuric acid may be replaced by alkanesulfonic acids on account of the improved performance properties of the latter.

Alkanesulfonic acids are also an alternative to phosphoric-acid-containing cleaning product formulations. Since methanesulfonic acid forms readily soluble salts and is readily biodegradable, it can play a role in water pollution control.

The production of alkanesulfonic acids initially generates crude alkanesulfonic acid. This is a mixture of alkanesulfonic acid, low boilers and high boilers. The low boilers and high boilers vary depending on the production process. Low boilers are generally water, nitric acid, hydrochloric acid, thioesters, alkanesulfonyl chloride, sulfur trioxide, alkanes and alkylsulfones. High boilers often include sulfuric acid, alkanesulfonic acids or chloroalkanesulfonic acid. Color-conferring substances may also be present.

To obtain pure alkanesulfonic acid or aqueous solutions of alkanesulfonic acid the crude alkanesulfonic acid is typically purified by distillation, nanofiltration, selective absorption of impurities over exchange resins or selective precipitation of impurities like salts. Of these, distillation is the dominant process, stripping being regarded as a distillative or evaporative process and distillation typically being performed at pressures below atmospheric pressure, since alkanesulfonic acid may form decomposition products at the temperatures required for distillation at atmospheric pressure. For example, distillative purification of methanesulfonic acid may lead to the formation of methyl methanesulfonate. A further problem is that methanesulfonic acid is corrosive at the high temperatures required for distillation and only a limited choice of stable construction materials is available.

WO-A 00/31027 discloses the production of alkanesulfonic acid by oxidation of alkyl mercaptans, dialkyldisulfides or dialkylpolysulfides with nitric acid. This generates nitrogen oxides, water and further byproducts such as sulfuric acid. The nitric acid is regenerated from the nitrogen oxides by oxidation with oxygen and recycled into the process. To purify the product, low boilers and high boilers are removed by distillation in two stages to obtain pure, practically anhydrous alkanesulfonic acid. Water and nitric acid are removed from the crude product in a water removal column operated as a stripping column at slightly reduced pressure. The bottoms product obtained comprises 1 wt % water and about 1 wt % high boiler, especially sulfuric acid. The removal of the high boilers is achieved by distillation of the alkanesulfonic acids yielding purities of greater than 99.5 wt % and sulfuric acid contents of less than 50 ppm under high vacuum, i.e. at a pressure of from 0.1 to 20 mbar (abs).

WO-A 2015/086645 describes the production of alkanesulfonic acid by oxidation of dialkyldisulfides with nitrogen oxides. The nitrogen oxides are regenerated with oxygen-enriched air for example. The reaction products are subsequently freed of low and high boilers via two distillation columns. The published process yields alkanesulfonic acid without any indication on its composition and specification.

GB-A 1350328 describes the synthesis of alkanesulfonic acids by chlorination of alkyl mercaptans or dialkyldisulfides in aqueous HCl. The product of the reaction is alkanesulfonic acid having a purity from 70 to 85 wt %. This document describes a two-stage process for producing anhydrous methanesulfonic acid. This comprises a first step in which water is distilled off and a second step in which the methanesulfonic acid is distilled out of the bottoms product in a short column and obtained at the top of the column.

WO-A 2005/069751 describes a methanation process which is the synthesis of methanesulfonic acid from sulfur trioxide and methane via a free-radical chain reaction with for example Marshall's acid as free-radical initiator in a methanation reactor. In this synthesis, anhydrous methanesulfonic acid is formed, but no information is given about purification. WO-A 2015/071365 describes a similar process, with distillation being suggested for purifying the resulting methanesulfonic acid. The product of this production process is mostly free of water. However, it might comprise sulfur trioxide.

CN-A 1810780 describes the synthesis of methanesulfonic acid by reaction of ammonium sulfite with dimethyl sulfate. This affords ammonium methylsulfonate and ammonium sulfate. Addition of calcium hydroxide forms soluble calcium methylsulfonate and insoluble calcium sulfate which may be removed easily. Sulfuric acid is added to liberate methanesulfonic acid and once again form and precipitate calcium sulfate. The aqueous solution formed is initially subjected to distillation to remove water and then subjected to distillation under reduced pressure to obtain methanesulfonic acid.

DE-C 197 43 901 describes the synthesis of methanesulfonic acid by reaction of sulfite ions with dimethyl sulfate. These sulfite ions are reacted in an aqueous system at elevated temperature and exposed to a strong acid. Sulfate is formed as a byproduct, for example in the form of sodium sulfate. Purification of the acid is by distillation.

EP-A 0 675 107 describes a process for continuous production of alkanesulfonyl chloride (ASC) or alkanesulfonic acid (ASA) by reacting an alkane mercaptan or a dialkanedisulfide with chlorine in aqueous hydrochloric acid at elevated pressure. Hydrogen chloride (HCl) and other low boilers not condensable under the process conditions are desorbed after being depressurized to atmospheric or subatmospheric pressure. ASC is produced at a preferred temperature range of from 10° C. to 35° C. and purified by means of a distillation column. ASA is obtained from ASC by hydrolysis at temperatures of from greater than 80° C. to 135° C. in the presence of water. The purification of ASC and/or ASA is also carried out with a vapor stripper for example, residual ASC also being hydrolyzed therein.

The removal of water from aqueous methanesulfonic acid by evaporation of the water in a falling film evaporator at reduced pressure is described in U.S. Pat. No. 4,450,047. Water is drawn off overhead and a product stream comprising more than 99.5 wt % methanesulfonic acid is obtained.

U.S. Pat. No. 4,938,846 discloses the removal of water from aqueous methanesulfonic acid by evaporation of the water in two falling-film evaporators arranged in series and both operated at reduced pressure.

The disadvantage of the prior art distillation processes is that these processes are highly energy intensive on account of the high temperatures and the required reduced pressure.

U.S. Pat. No. 4,035,242 discloses a likewise very energy intensive process where aqueous methanesulfonic acid is purified in a two-stage distillation process. In the first distillation column a large part of the water is removed as a low boiler at reduced pressure. The bottoms product comprising methanesulfonic acid is evaporated and separated in a second rectification column at reduced pressure to obtain the methanesulfonic acid.

U.S. Pat. No. 6,337,421 discloses the removal of sulfuric acid from methanesulfonic acid using basic anion exchange resins. Other processes of removing sulfuric acid are also described, for example distillation or fractionating crystallization and also separation by nanofiltration, but none of these achieve adequate results according to the description of U.S. Pat. No. 6,337,421.

The purification of methanesulfonic acid comprising oxidizable compounds is described in EP-A 0 505 692 and EP-A 0 373 305. EP-A 0 505 692 discloses supplying chlorine to convert the impurities into methanesulfonyl chloride which is hydrolyzed to afford methanesulfonic acid and HCl in a further step. EP-A 0 373 305 discloses supplying ozone which converts methyl thiosulfate into methanesulfonic acid. However, the disadvantage of these two processes is that high-boiling components such as sulfuric acid cannot be removed, thus necessitating further purification steps.

The fractionating crystallization of methanesulfonic acid and also of ethanesulfonic acid is known in principle from R. A. Craig et al., J. Am. Chem. Soc., 1950, Vol. 72, pages 163 to 164 or A. Berthoud, Helv. Chim. Acta, 1929, Vol. 12, page 859, but no indication is given as to how the processes described therein could be implemented in production and purification processes on a large industrial scale.

I. Sandemann, J. Chem. Soc., 1953, page 1135 describes that methanesulfonic acid and sulfur trioxide form a crystallizable complex of a mixed anhydride of methanesulfonic acid and sulfuric acid. According to Sandemann the separated solid comprises three molecules methanesulfonic acid and one molecule sulfur trioxide. The methanesulfonic acid is formed from the complex by adding water.

The formation of methanesulfonic anhydride by reaction of methanesulfonic acid with sulfur trioxide is described by E. A. Robinson and V. Silberberg in Can. J. Chem., Vol. 44, 1966, page 1438. Depending on the concentration ratio polymers of the formula $(CH_3)_2S_{n+1}O_{3n+5}$ are formed. The reaction products have been analyzed by NMR spectroscopy and Raman spectroscopy. All of the reactions are equilibrium reactions.

However, all of these documents show processes for producing and/or purifying alkanesulfonic acid. Producing pure alkanesulfonic acid by a known process needs large amounts of energy.

It has been an object of the present invention to provide a process for purifying alkanesulfonic anhydride and further a process for producing alkanesulfonic acid which is less energy intensive than prior art processes and which can be implemented on a large industrial scale.

This object is achieved by a process for purifying alkanesulfonic anhydride which comprises the following steps of:
(a) feeding a stream comprising alkanesulfonic anhydride, sulfuric acid, high boilers and residual low boilers into a melt crystallization to form crystals of the alkanesulfonic anhydride suspended in mother liquor,
(b) performing a solid-liquid separation to remove the crystals from the mother liquor,
(c) optionally washing the crystals to remove mother liquor adhering to the crystals.

Surprisingly it has been found that it is possible to remove impurities like sulfuric acid, high boilers and low boilers by a melt crystallization with much lower energy consumption than by distillation processes.

Another advantage is that, in contrast to hitherto employed processes of distillative purification, the process according to the invention allows to achieve high purities in simple fashion.

In context of the present invention the term alkanesulfonic anhydride is used for the reaction product which is formed together with sulfuric acid by reaction of alkanesulfonic acid and sulfur trioxide and which solidifies during cooling of the liquid reaction system. Depending on the reaction conditions besides pure alkanesulfonic anhydride also a complex of pure alkanesulfonic anhydride and sulfur trioxide can be formed. In this case the term "alkanesulfonic anhydride" also includes this complex.

According to the present invention, a low boiler is a component in a mixture of chemical substances whose vapor pressure is higher than the vapor pressure of other components in the mixture. The complement of a low boiler is a high boiler which is a component in a mixture of chemical substances whose vapor pressure is lower than the vapor pressure of other components in the mixture. The defined terms are used in the thermal separation technology. Low boilers are withdrawn from a separation column at the top. High boilers are withdrawn from a separation column at the bottom.

The stream comprising alkanesulfonic anhydride, alkanesulfonic acid, sulfuric acid, high boilers and residual low boilers for example originates from a process where an alkane, particularly methane, and sulfur trioxide are brought into reaction forming alkanesulfonic anhydride, particularly methane sulfonic anhydride. From the reaction a crude alkanesulfonic anhydride is obtained. Depending on the reaction process the crude alkanesulfonic anhydride additionally may contain byproducts as impurities. As low boilers particularly alkanes, inert gases, sulfur dioxide and sulfur trioxide which have not reacted can be contained in the crude alkanesulfonic anhydride.

In an embodiment of the invention, the stream comprising alkanesulfonic acid, sulfuric acid, high boilers, residual low boilers and the alkanesulfonic anhydride is produced by the reaction of alkanesulfonic acid with sulfur trioxide. The alkanesulfonic acid in this case for example originates from a conventional process for producing alkanesulfonic acids. Appropriate processes are described in WO-A 00/31027, GB-A 1350328, EP-A 0 675 107, ON-A 1810780 or WO-A 2015/071365 for example. In all processes crude alkanesulfonic acid is produced and depending on the production process employed the crude alkanesulfonic acid comprises different low boilers and high boilers as impurities.

To remove the low boilers, it is preferred to carry out a distillation or stripping process step before feeding the stream comprising alkanesulfonic anhydride, alkanesulfonic acid, sulfuric acid, high boilers and residual low boilers into the melt crystallization. For the distillation, a crude product stream is fed into a distillation apparatus or stripping apparatus, the crude product stream comprising alkanesulfonic anhydride, sulfuric acid, high boilers and low boilers. The crude product stream in these cases originates from any suitable process for producing alkanesulfonic anhydride.

When the stream comprising alkanesulfonic anhydride, sulfuric acid, high boilers and residual low boilers originates from a reaction of alkanesulfonic acid and sulfur trioxide, it is particularly preferred to carry out a distillation for removing low boilers from the crude alkanesulfonic acid before the reaction is performed. The process for producing and purifying alkanesulfonic anhydride preferably comprises:

(i) optionally distilling a melt comprising crude alkanesulfonic acid to completely or partly remove low boilers obtaining a material stream comprising alkanesulfonic acid, high boilers and residual low boilers,
(ii) feeding the material stream comprising alkanesulfonic acid, high boilers and residual low boilers as a first stream and sulfur trioxide as a second stream into a reaction stage where the alkanesulfonic acid reacts with the sulfur trioxide forming alkanesulfonic anhydride,
(iii) purifying the alkanesulfonic anhydride.

Low boilers in the crude alkanesulfonic acid, include, for example, short-chain hydrocarbons having 1 to 8 carbon atoms, short-chain alcohols having 1 to 8 carbon atoms, nitric acid, hydrochloric acid, chlorine, alkyl mercaptans, dialkylsulfides, dialkyl disulfides, dialkyl polysulfides, esters, for example methyl methanesulfonate, methyl methanethiosulfonate, partly and fully chlorinated alkanesulfonic acids, methanesulfonyl chloride, sulfur dioxide, ammonia, dimethyl sulfate, monomethyl sulfate, dimethylsulfoxide and dimethyl sulfone. The process for producing alkanesulfonic acid described in WO-A 00/31027 typically generates water, alkyl mercaptans, dialkyl disulfides, dialkyl polysulfides, alkyl alkanethiosulfonates such as methyl methanethiosulfonate, alkyl alkanethiosulfinates, dialkyl disulfoxide, $C_1$-$C_x$-alcohols, nitric acid, nitrogen oxides, methyl methanesulfonate and sulfur dioxide as low boilers. Typical low boilers in the process described in GB-A 1350328 are water, alkyl mercaptans, dialkyl disulfides, dialkyl polysulfides, alkyl alkanethiosulfonates such as methyl methanethiosulfonate, alkyl alkanethiosulfinates, dialkyl disulfoxides, alkanesulfonyl halides such methanesulfonyl chloride, halogens such as chlorine or bromine, hydrogen halides such as hydrogen chloride or hydrogen bromide, Chalogenated methanesulfonic acid compounds, methyl methanesulfonate and sulfur dioxide. Low boilers typically present in the process described in CN-A 1810780 are water, ammonia, methanol, dimethyl sulfate, monomethyl sulfate, hydrogenchloride, sulfur dioxide and methyl methanesulfonate. In the production processes that are not water-free, water generally forms the largest proportion of the low boilers.

In water-free production processes for alkanesulfonic acids or production processes of alkanesulfonic anhydride, examples of conventional low boilers are short-chain hydrocarbons having 1 to 8 carbon atoms, sulfur trioxide, sulfur dioxide, impurities from feedstocks, e.g. from the alkane used, initiators and the decomposition products thereof and by-products of the reaction, for example carbon monoxide or carbon dioxide.

Low boilers in the alkanesulfonic anhydride correspond to those in the alkanesulfonic acid. However, as compounds with acidic active hydrogen, like water, alcohols and mercaptans, immediately react with sulfur trioxide or alkanesulfonic anhydride, only reaction products of these compounds are contained as impurities in the crude alkanesulfonic anhydride. The reaction products thereby can be either low boilers or high boilers.

As water immediately reacts with alkanesulfonic anhydride forming alkanesulfonic acid, it is preferred to avoid adding water containing material in the process. Particularly in processes for producing the alkanesulfonic acid which are not water-free, it is preferred to remove as much water as possible before feeding into the reaction stage in step (ii). In these cases the water is removed as a low boiler in the distillation step (i)

Due to the production processes of alkanesulfonic anhydride the low boilers in streams comprising alkanesulfonic anhydride particularly comprise sulfur trioxide.

High boilers present in the crude alkanesulfonic anhydride or the crude alkanesulfonic acid generally include sulfuric acid, alkanedisulfonic acids, long-chain hydrocarbons, inorganic salts such as sodium sulfate, sodium hydrogensulfate, sodium methylsulfate, ammonium sulfite, ammonium methylsulfate, calcium hydroxide, calcium sulfate, calcium methylsulfate and alkanesulfonic acids or alkanesulfonic anhydrides having more carbon atoms than the target product. In crude alkanesulfonic anhydride, additionally alkanesulfonic acid may be contained as a high boiler. As in the case of the low boilers, the high boilers present in the crude alkanesulfonic acid also depend on the production process. Thus, for example, sulfuric acid in particular is present as a high boiler in the processes described in WO-A 00/31027, in DE-C 197 43 901 and in GB-A A 1350328.

In a number of production processes, for example the process described in WO 2004/101860, dialkylpolysulfides may also be present, these occurring as high boilers or low boilers depending on their sulfur content. By contrast, the crude alkanesulfonic acid produced by the process according to CN-A 1810780 comprises ammonium sulfite, ammonium sulfate, ammonium salts of alkanesulfonic acid, calcium salts of alkanesulfonic acid, sulfuric acid, calcium sulfate and ammonium hydrogensulfate as high boilers.

It is a further advantage of the complete or partial removal of the low boilers via distillation that the melting point of the starting melt of the stream comprising alkanesulfonic anhydride, alkanesulfonic acid, sulfuric acid, high boilers and residual low boilers for the subsequent melt crystallization is higher than before distillation. The starting melt consequently requires less intense cooling, thus allowing cooling energy savings to be made.

The crystallization allows removing the impurities in the stream comprising alkanesulfonic anhydride, sulfuric acid, high boilers and residual low boilers. Said impurities accumulate in the mother liquor during the crystallization.

Since a crystallization and subsequent solid-liquid separation cannot generally achieve complete removal of the product from the starting melt, the mother liquor exiting the crystallizer still comprises a large proportion of product. It is therefore preferred that the alkanesulfonicanhydride-depleted mother liquor exiting the crystallizer is completely or at least partly recycled back into the process for purifying alkanesulfonic anhydride. Preferably, the mother liquor is recycled completely. Here, the alkanesulfonic-anhydride-depleted mother liquor preferably is passed back into the crystallizer, referred to as the crystallization cycle. Alternatively, it is also possible to recycle the alkanesulfonic-anhydride-depleted mother liquor back into the reactor for producing the alkanesulfonic acid, referred to as reactor cycle or to recycle the mother liquor in the initiator production, referred as the initiator cycle.

When the washing of the crystals in step (c) is additionally carried out, impurified washing liquid is generated which is recycled into the process for purifying alkanesulfonic anhydride. In this case, it is preferable when the washing liquid is combined with the mother liquor and is then recycled according to the options named above.

Since crystallization of the alkanesulfonic anhydride causes high boilers to accumulate in the mother liquor particularly in the case of recycling into the melt crystallization, it is moreover preferable when the mother liquor removed in step (b) is at least partly drained.

As the mother liquor which is drained from the process still comprises alkanesulfonic acid and alkanesulfonic anhydride, it is preferred to further proceed the drained mother liquor. For this purpose it is possible for example to feed the drained mother liquor into a distillation column in which alkanesulfonic acid and alkanesulfonic anhydride are separated off and recycled into the process. High boilers and low boilers, separated off in this process step are removed.

All distillation steps preferably are carried out at a pressure below atmospheric pressure. It is particularly preferable when the distillations are carried out at a pressure in the range from 5 to 500 mbar (abs), preferably from 10 to 100 mbar (abs). This allows for distillation/evaporation that is gentle toward the alkanesulfonic anhydride product. At higher pressures the necessary temperatures for the distillation/evaporation would be of a magnitude such that product impairment, in particular decomposition of the alkanesulfonic anhydride, cannot be ruled out. It is known that distillation processes using entraining agents, so-called stripping processes, may be carried out at higher pressures. This procedure is regarded as equivalent to the use of subatmospheric pressure in the context of the invention.

The distillations may be performed in any desired distillation device known to those skilled in the art. The distillation is typically carried out in a distillation column which may comprise internals. Typical internals include, for example, trays or structured or unstructured packings. Useful trays include all known trays, for example sieve trays, bubble trays, tunnel trays or valve trays. Structured packings may be, for example, those made of ceramics materials or plastics materials such as PTFE or PFA. Unstructured packings are, for example, random packings, wherein all commonly used packing elements may be employed, for example those made of ceramics materials, plastic materials such as PTFE or PFA.

The crude alkanesulfonic anhydride or the crude alkanesulfonic acid from the production is generally introduced near the top of the distillation column to separate dominating low boilers.

The low boilers are removed overhead and sent for workup or disposal. A material stream comprising alkanesulfonic acid or alkanesulfonic anhydride, high boilers and residual low boilers, in particular sulfur trioxide is withdrawn at the bottom of the distillation column.

In embodiments where crude alkanesulfonic anhydride is distilled for removing low boilers, a stream comprising alkanesulfonic anhydride, high boilers and low boilers is withdrawn from the distillation and fed into the melt crystallization as the starting melt.

The starting melt is generally a monophasic liquid. This means that the alkanesulfonic anhydride too is completely comprised in the liquid phase.

Generally, the distillation for removing low boilers and the melt crystallization are carried out at different temperatures. Thus, it is necessary, irrespective of the distillation device employed, to cool the material stream comprising alkanesulfonic anhydride, high boilers and residual low boilers before it is fed into the melt crystallization. Even when the low boilers removal is carried out at, for example, a subatmospheric pressure of 100 mbar (abs) it is necessary to carry out the distillation with heating in order to establish a bottoms temperature in the range from 50° C. to 130° C. Since the melting point of an alkanesulfonic anhydride mixture is in the range from 0° C. to 70° C. depending on the content of other components (e.g. methanesulfonc acid), appropriate cooling of the bottoms discharge preferably to a temperature just above the melting point of the starting melt must first be effected. Alternatively, it is also possible to supercool the melt before entry into the crystallizer. However, such a mode of operation is not preferred since it is difficult to rule out unwanted crystallization in a heat exchanger. The temperature which has to be chosen additionally depends on the alkanesulfonic anhydride which is purified.

The distillation for removing low boilers preferably frees the crude alkanesulfonic anhydride or the crude alkanesulfonic acid of low boilers to such an extent that, in processes being water-free, the proportion of impurities in the material stream comprising alkanesulfonic anhydride, high boilers and residual low boilers sent to the melt crystallization as the starting melt has a concentration of alkanesulfonic anhydride of more than 20 mol % and a melting point of 10 to 20° C. depending on the content of other components. It is particularly preferable when the proportion of alkanesulfonic anhydride is more than 75 mol %. These indications are merely typical values which moreover depend on the alkanesulfonic acid production process and the high boilers content.

If the crude alkanesulfonic anhydride origins from a reaction of alkanesulfonic acid with sulfur trioxide, the proportion of alkanesulfonic anhydride to sulfuric acid is 50 mol % to 50 mol % due to the reaction stoichiometry. Therefore, in these cases the concentration of alkanesulfonic anhydride in the starting melt generally is in the range between 40 and 50 mol %.

In contrast to the distillation which is carried out at a pressure below atmospheric pressure, the melt crystallization is generally effected at atmospheric pressure. The temperature depends on the alkanesulfonic anhydride to be crystallized and preferably the melt crystallization is carried out at a temperature in the range from 0° C. to 70° C. If the alkanesulfonic anhydride is methanesulfonic anhydride, the temperature at which the crystallization is carried out preferably is in the range from 10° C. to 40° C. and in particular in the range from 20° C. to 30° C. For ethanesulfonic acid, the crystallization preferably is carried out at temperature in the range from 0 to 20° C. and in particular in the range from 10 to 20° C. Crystallization temperatures near ambient temperature are preferred since they entail lower energy requirements for the crystallization.

The optimal crystallization conditions may vary depending on the type and concentration of the impurities and the used solvent. Said conditions should accordingly be determined by experiment for example.

The crystallizer in which the melt crystallization is carried out may be any apparatus suitable for performing a crystallization. Heat may be removed from the crystallizer by, for example, jacket cooling or by suitable internals, for example pipes through which a coolant flows, until a temperature low enough for crystallization is achieved. An example of a suitable coolant which in the case of jacket cooling flows through a double wall of the crystallizer or is employed in the internal pipes is a mixture of water and ethylene glycol. It is alternatively possible to carry out direct cooling by means of an evaporating coolant, for example carbon dioxide.

In one embodiment, namely the suspension crystallization method, cooling in the crystallizer converts the starting melt into a suspension comprising alkanesulfonic anhydride crystals. To achieve this, solid crystals of alkanesulfonic anhydride may grow directly in the melt thus forming the suspension or alternatively the solid crystals may deposit on a cooled wall from which they are subsequently scraped off and resuspended in the mother liquor. Suitable apparatuses include, for example, stirred tanks, scraped surface coolers or disk crystallizers.

An alternative embodiment comprises carrying out a layer crystallization. Here, the crystallizate is formed as an uninterrupted adherent layer on a cooled surface of the crystallizer. In this case the solid-liquid separation is effected by flow-off of the mother liquor under gravity. The layer crystallization may be carried out either as a static layer crystallization or as a dynamic layer crystallization.

In static layer crystallization the starting melt is charged into a suitable heat exchanger, for example a tube bundle heat exchanger or a plate heat exchanger, and cooled by gradual temperature reduction to partly solidify the starting melt. In a further step the mother liquor is drained and the temperature is increased again. This initially melts off a highly impurified fraction from the crystal layer before the product is melted off in high purity. However, the disadvantage of the static crystallization method is the typically low space-time yield since heat and material transport to the deposition surfaces is effected only by free convection. By contrast, dynamic layer crystallization comprises establishing forced convection by pumped circulation of the mother liquor through the pipes, by introduction as a trickle film, by introducing inert gas into a pipe filled with mother liquor or by pulsing.

In suspension crystallization a suspension in which the crystals are suspended in the mother liquor is withdrawn from the crystallizer. Since alkanesulfonic anhydride is crystallized out of the starting melt the proportion of molten alkanesulfonic anhydride in the mother liquor withdrawn from the crystallizer is lower than that in the starting melt supplied to the crystallizer. The concentration of impurities in the mother liquor is also higher since these largely do not crystallize. Only the liquid portion, i.e. the liquid phase of the suspension, is referred to as mother liquor.

In order to remove the mother liquor and impurities adhering to the crystals it is possible and preferable to wash the crystals in step (c). This comprises contacting the crystals with a washing liquid with which the impurities are removed.

Any suitable washing means may be used to wash the crystals in step (c). It is possible to employ a separate washing means or to carry out the solid-liquid separation and washing in one apparatus. A suitable apparatus is, for example, a washing column. In the washing column the crystals to be purified and the washing liquid are preferably run in countercurrent.

Since the starting melt comprising alkanesulfonic anhydride is corrosive it is necessary to configure not only the production apparatuses but also the crystallizer, the apparatus for solid-liquid separation and the washing means in such a way that they are stable against process conditions. It is in particular necessary to avoid the alkanesulfonic anhydride becoming contaminated by corroded and detached constituents of the apparatus. Suitable corrosion-resistant materials that may be used to fabricate the washing means include, for example, glasses, corrosion resistant steels, enameled steels or plastics materials. Theses materials all can be used either as construction material which means that apparatuses are fully made of that materials or as a lining. In this case the apparatuses are coated with these materials on the surfaces which can be in contact with the alkanesulfonic acid or alkanesulfonic anhydride. Plastics materials may be employed either as facing materials or in a load-bearing capacity. Suitable plastics materials are, for example, high density polyethylene (HDPE), polypropylene (PP) or PTFE. Plastics materials either can be used as a construction material to provide corrosion or for thermal insulation of the outer surface of the apparatus. It is possible that some apparatus parts may be under too high a level of mechanical stress for plastics materials. Construction may then be effected in such a way that the stressed plant parts are fabricated from, for example, mechanically stable, enameled steel, or corrosion resistant steels.

Useful washing liquids include, for example, alkanesulfonic acid, sulfuric acid or other solvents and combinations thereof. However, all of these have the disadvantage that the crystals of alkanesulfonic anhydride may be dissolved. Moreover, impurities may also be introduced. It is therefore preferable to employ molten crystallizate as the washing solution instead of the abovementioned washing liquids. The molten crystallizate removes the mother liquor adhering to the crystals and the impurities. Since the molten crystallizate employed as the washing liquid becomes impurified by the mother liquor and by the impurities that are washed off from the crystals and the washing liquid comprises a large proportion of product of value on account of its composition, it is preferable when the molten crystallizate employed as the washing liquid is recycled into the crystallization cycle. An alternative washing liquid would be a mixture of the alkanesulfonic anhydride and the alkanesulfonic acid if sufficiently pure.

When molten crystallizate is used as the washing liquid some of the washing liquid generally also crystallizes on the crystals to be purified.

In order to avoid sedimentation of the crystals from the suspension during transport between the individual apparatuses, in particular between the crystallizer and the washing means, it is preferable to homogenize the suspension. This may be achieved by using stirrers or pumps for example.

The washing means may either be directly supplied with the suspension withdrawn from the crystallizer while an alternative option comprises subjecting the suspension to processing before it is fed into the washing means. This comprises initially removing the crystals suspended in the mother liquor by mechanical means. This may be achieved using any known separation method for solid-liquid separations. Suitable separation methods include, for example, sieving, pressing, filtration, centrifugation, sedimentation and decantation. After removal of the mother liquor the crystals are resuspended in the washing liquid and the suspension is fed into the washing means.

When molten crystallizate is employed as washing liquid it is preferable when the temperature is selected such that the molten crystallizate for washing the crystals has a temperature 0.1° C. to 15° C. above the solidification temperature of the alkanesulfonic-anhydride-containing crystallizate. It is preferable when the temperature of the crystallizate employed as washing liquid is 1° C. to 10° C. above the solidification temperature of the alkanesulfonic anhydride and in particular 2° C. to 4° C. above the solidification temperature of the alkanesulfonic anhydride.

The washing means is preferably operated such that the residence time of the crystals to be washed in the washing means is in the range from 0.1 to 25 min. and preferably in the range from 1 to 15 min. However, particularly but not exclusively when the suspension comprising crystals and the molten crystallizate washing liquid are run in countercurrent it has been found that sufficient purification efficacy is achieved even with a residence time of 2 to 8 min.

The crystals may be washed repeatedly to improve purification efficacy. To this end, the washing in step (c) or else the sequence comprising crystallization in step (a), solid-liquid separation in step (b) and washing in step (c) may be performed repeatedly or operated with partial recycling. However, preference is given to performing crystallization and washing just once. The washing of the crystals may even be eschewed when product purity requirements are low.

The three cited material stream cycles, namely the reactor cycle, crystallization cycle and initiator cycle pass through plant sectors which in some cases have very different temperature levels. In order to make good use of the energy introduced into the process while furthermore keeping the amount of energy required for heating and cooling the material streams as low as possible it is preferable when the material stream cycles are passed through heat exchangers which transfer heat in countercurrent. For example, the material stream withdrawn from the bottoms discharge of the low boilers distillation and comprising alkanesulfonic anhydride, high boilers and residual low boilers is cooled before being fed into the melt crystallization while, conversely, the alkanesulfonic-anhydride-depleted mother liquor recycled into the distillation is heated. It is thus particularly preferable when heat is transferred from the material stream comprising alkanesulfonic anhydride, high boilers and residual low boilers which is to be cooled to the alkanesulfonic-anhydride-depleted mother liquor which is to be heated.

When efficient crystallization and washing processes are available, the low boilers and high boilers may be accumulated to high concentrations in the reactor cycle, i.e. in the recirculating mother liquor, without the crystallized alkanesulfonic anhydride failing to meet industry purity specifications.

The process can be used for purifying any alkanesulfonic anhydride. However, preferably the alkanesulfonic anhydride is methanesulfonic anhydride or ethanesulfonic anhydride and particularly the alkanesulfonic anhydride is methanesulfonic anhydride.

The purified alkanesulfonic anhydride particularly can be used for producing alkanesulfonic acid. It is possible to either produce anhydrous alkanesulfonic acid or aquous solutions of alkanesulfonic acid in any concentration by adding various quantities of water.

A process for producing anhydrous alkanesulfonic acid from alkanesulfonic anhydride, comprises:
purifying alkanesulfonic anhydride according to the above defined process or producing and purifying alkanesulfonic anhydride according to the above defined process,
solving the crystals in a water-containing alkanesulfonic acid, wherein the water of the water-containing alkanesulfonic acid reacts with the alkanesulfonic anhydride forming alkanesulfonic acid or mixing equimolar amounts of the alkanesulfonic anhydride and water wherein the water reacts with the alkanesulfonic anhydride forming alkanesulfonic acid.

By this process it is particularly possible to produce pure alkanesulfonic acid in a manner which is less complex than those processes as known in the art, where the pure alkanesulfonic acid is gained by distillation. Particularly it is possible by this process to gain alkanesulfonic acid which is completely free from water. Completely free of water in this context means that the amount of water in the alkanesulfonic acid is less than 0.001 wt %.

According to the present invention, pure alkanesulfonic acid or anhydrous alkanesulfonic acid means that the proportion of impurities and water is less than 1 wt %, preferably less than 0.5 wt % and in particular less than 0.2%.

In one embodiment the water-containing alkanesulfonic acid for example emanates from a production and purification process of alkanesulfonic acid which comprises 0.5 to 13 mol % water, more preferably 0.5 to 8 mol % water and particularly preferred 0.5 to 7 mol % water. If the alkanesulfonic acid is methanesulfonic acid, it is particularly preferred when the water-containing methanesulfonic acid comprises 96 mol % methanesulfonic acid and 4 mol % water. However, besides using alkanesulfonic acid comprising 0.5 to 13 mol % water it is also possible to use the monohydrate of the alkanesulfonic acid as water-containing alkanesulfonic acid which generally comprises 50 mol % water. As the monohydrate may comprise water excess or water shortage, the monohydrate may comprise 47 to 53 mol % water and particularly preferred 49 to 51 mol % water. The hydrates of alkanesulfonic acids are easily gained by crystallization from aqueous solution of alkanesulfonic acid. The hydrates are therefore preferred reactants with alkanesulfonic anhydride.

To obtain pure alkanesulfonic acid the amounts of alkanesulfonic anhydride and watercomprising alkanesulfonic acid are preferably chosen such that all of the water reacts with alkanesulfonic anhydride forming alkanesulfonic acid and further there is no excess of alkanesulfonic anhydride or water. This allows for producing pure alkanesulfonic acid without an additional distillation for removal of impurities.

For producing water-containing alkanesulfonic acid, it is either possible to add a larger amount of water-containing alkanesulfonic acid or to add the monohydrate of the alkanesulfonic acid to gain alkanesulfonic acid comprising a smaller amount of water. Further it is possible to achieve alkanesulfonic acid with any water content by simply adding water.

A process for producing peroxoalkanesulfonic acid comprises:
purifying alkanesulfonic anhydride as described above or producing and purifying alkanesulfonic anhydride according as described above,
adding the purified alkanesulfonic anhydride to a mixture comprising water and hydrogen peroxide, wherein the hydrogen peroxide reacts with the alkanesulfonic anhydride forming peroxoalkanesulfonic acid and the water reacts with the alkanesulfonic anhydride forming alkanesulfonic acid.

The peroxoalkanesulfonic acid can be used e.g. as radical starter for the activation of alkane in an alkanation process to produce alkanesulfonic acid or alkanesulfonic anhydride.

As a further alternative, it is also possible to add sulfuric acid to the alkanesulfonic anhydride. In this case, the sulfuric acid reacts with the alkanesulfonic anhydride forming alkanesulfonic acid and sulfur trioxide. The sulfur trioxide then preferably is used as reactant in the production of the alkanesulfonic anhydride. Such a process comprises:

purifying alkanesulfonic anhydride as described above or producing and purifying alkanesulfonic anhydride as described above, adding the alkanesulfonic anhydride to a mixture comprising sulfuric acid, wherein the sulfuric acid reacts with the alkanesulfonic anhydride forming alkanesulfonic acid and sulfur trioxide.

The alkanesulfonic acid can be added either as a solid or as a liquid.

The reaction of the sulfuric acid with the alkanesulfonic acid preferably is carried out at elevated temperature in the range from 50° C. to 200° C. and low pressure in the range from 50 to 500 mbar to support the reaction.

The mixture comprising sulfuric acid either is aqueous sulfuric acid or a mixture of sulfuric acid and a solvent or preferably a mixture of sulfuric acid and alkanesulfonic acid. The alkanesulfonic acid in this case preferably corresponds to the alkanesulfonic anhydride. In case of methanesulfonic anhydride, the alkanesulfonic acid preferably is methanesulfonic acid.

In a preferred embodiment, the sulfur trioxide is recycled into the production process of crude alkanesulfonic acid or into the production process of alkanesulfonic anhydride.

The inventive process for purifying alkanesulfonic anhydride preferably is used for purifying methanesulfonic anhydride or ethanesulfonic anhydride, particularly for purifying methanesulfonic anhydride.

The alkanesulfonic acid produced by the process using the alkanesulfonic anhydride, thus preferably is methanesulfonic acid or ethanesulfonic acid, particularly methanesulfonic acid.

Exemplary embodiments of the invention are shown in the figures and are illustrated in more detail in the following description.

Figure 1:
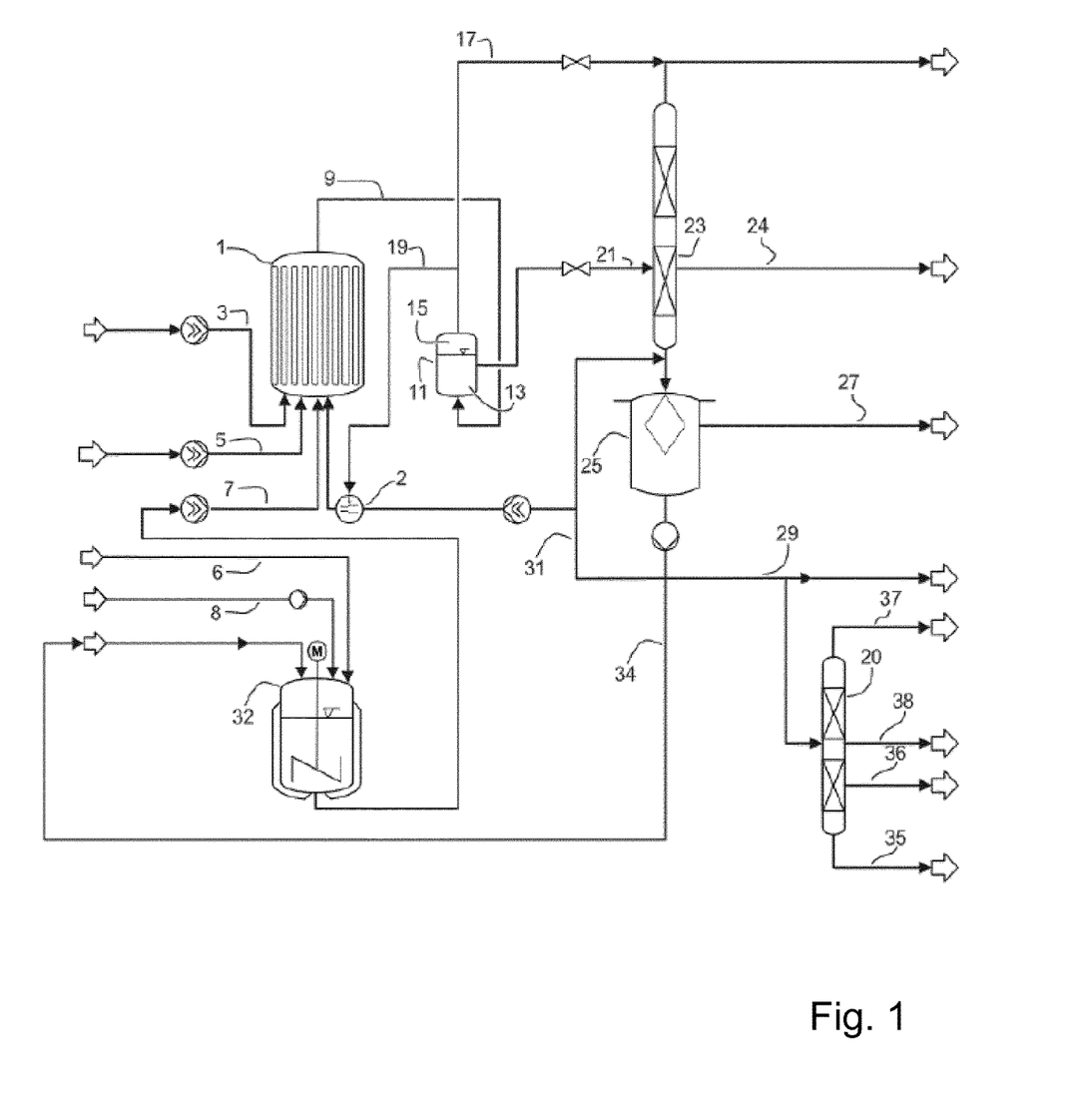
FIG. 1 shows a process for producing and purifying alkanesulfonic anhydride including a methanation reactor.

A process for producing and purifying alkanesulfonic anhydride including a methanation reactor is shown in FIG. 1.

A reactor 1 is provided with a first inlet 3, a second inlet 5 and a third inlet 7. The first inlet 3 is connected with a sulfur trioxide source, the second inlet 5 with a source for purified alkane, preferably purified methane, and the third inlet 7 with a source for an initiator.

Via the inlets 3, 5, 7 sulfur trioxide, alkane and initiator are fed into the reactor 1. In the reactor, alkanesulfonic anhydride is formed by reaction of alkane and sulfur trioxide. The reaction mixture from the reactor is fed via a line 9 into a phase separator 11. In the phase separator 11 a liquid phase 13 is separated from a gaseous phase 15. The liquid phase 13 contains alkanesulfonic anhydride, sulfuric acid, low boilers and high boilers. A part of the gaseous phase 15 is withdrawn from the process via line 17 and the rest of the gaseous phase 15 is recycled into the reactor 1 via line 19 driven by a pumping device for instance an injector system 2.

The liquid phase 13 is fed into a distillation column 23 via line 21. In the distillation column, low boilers are removed from the liquid phase. The low boilers are removed at the top of the distillation column 23 and withdrawn from the process via line 17. The remaining liquid stream comprising alkanesulfonic anhydride, sulfuric acid, high boilers and residual low boilers is fed into a crystallization apparatus 25.

In the crystallization apparatus 25 crystals of the alkanesulfonic anhydride suspended in mother liquor are formed. The crystals of alkanesulfonic anhydride are withdrawn via a product line 27. The remaining mother liquor is partly removed via a purge line 29. At least a part of the rest of the mother liquor is recycled into back into the reactor 1 via a recycle line 31 (reactor cycle).

The initiator preferably is produced in an initiator reactor 32. A suitable initiator for example is a mixture comprising sulfuric acid, alkanesulfonic acid, preferably methanesulfonic acid, sulfur trioxide and hydrogen peroxide. In this case sulfur trioxide is added into the initiator reactor 32 via a sulfur trioxide inlet 8 and the hydrogen peroxide via a hydrogen peroxide inlet 6. Via further inlets not shown in FIG. 1, sulfuric acid and alkanesulfonic acid are added to the initiator reactor. From the initiator reactor 32 the initiator is fed into the reactor 1 via the third inlet 7.

In an alternative embodiment as shown in FIG. 1, the initiator is produced in the initiator reactor 32 from alkanesulfonic anhydride. In this case at least a part of the mother liquor is recycled into the initiator reactor 32 from the crystallization apparatus 25 via line 34 (initiator cycle). Additionally, sulfur trioxide and hydrogen peroxide are fed into the initiator reactor 32 via the sulfur trioxide inlet 8 and the hydrogen peroxide inlet 6. In the initiator reactor 32 the alkanesulfonic acid reacts with the sulfur trioxide forming alkanesulfonic acid and sulfuric acid. The thus produced initiator the is fed into the reactor 1 via the third inlet 7.

As the mother liquor comprises valuable components, for instance alkanesulfonic acid and alkanesulfonic anhydride, the part of the mother liquor removed via the purge line 29 is fed into a distillation column 20 to gain the valuable components. In the distillation column 20 alkanesulfonic acid is withdrawn via a first side outlet 38 and alkanesulfonic anhydride via a second side outlet 36 which is at a lower position than the first side outlet 38. Volatiles are removed at the top of the distillation column 20 via a top line 37 and high boilers are removed from the bottom via a bottom line 35. The volatiles and high boilers withdrawn from the distillation column 20 are discarded.

Figure 2:
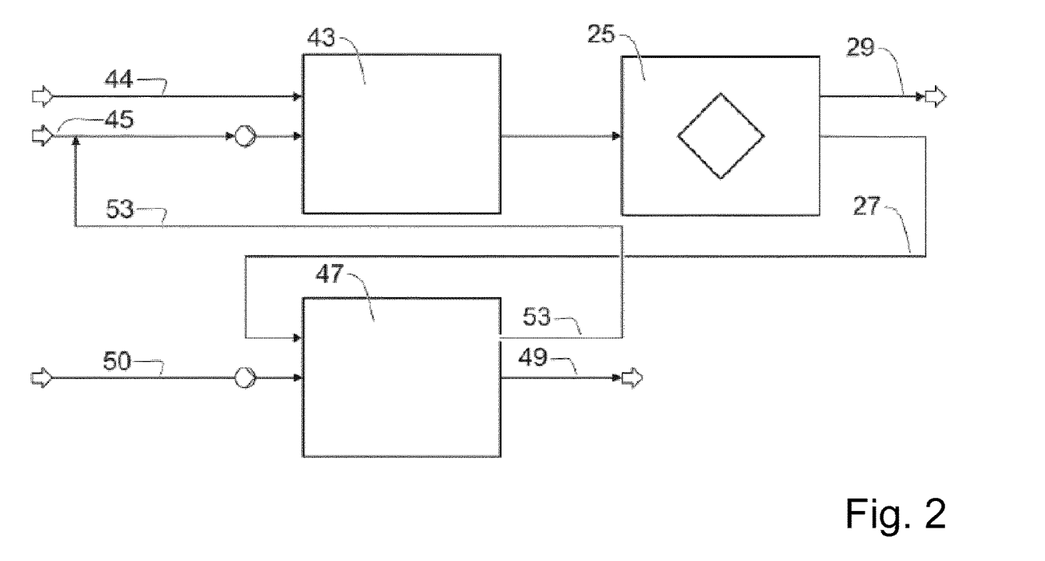
FIG. 2 shows a process overview for a process for producing alkanesulfonic anhydride from crude alkanesulfonic acid, purifying the alkanesulfonic anhydride and regaining the alkanesulfonic acid by reaction with sulfuric acid.

FIG. 2 shows a process overview for a process for producing alkanesulfonic anhydride from crude alkanesulfonic acid, purifying the alkanesulfonic anhydride and regaining the alkanesulfonic acid by reaction with sulfuric acid.

A crude alkanesulfonic acid 44, comprising high boilers and low boilers besides the alkanesulfonic acid is fed into a reaction step 43. Additionally, via an inlet line 45 sulfur trioxide is fed into the reaction step 43. In the reaction step 43 the alkanesulfonic acid reacts with the sulfur trioxide forming alkanesulfonic anhydride and sulfuric acid. From the reaction step 43 crude alkanesulfonic anhydride is withdrawn. The crude alkanesulfonic anhydride comprising alkanesulfonic anhydride, sulfuric acid, high boilers and low boilers is fed into a melt crystallization 25, where crystals of alkanesulfonic anhydride suspended in mother liquor are formed. The mother liquor comprising sulfuric acid is removed via the purge line 29. The alkanesulfonic anhydride is withdrawn from the crystallization 25 via product line 27 and fed into a second reaction step 47. Via an inlet 50 sulfuric acid is fed into the second reaction step 47. In the second reaction step the alkanesulfonic anhydride reacts with the sulfuric acid forming alkanesulfonic acid and sulfur trioxide. In the second reaction step 47 the sulfur trioxide is separated from the alkanesulfonic acid by evaporation. The alkanesulfonic acid is removed as liquid product 49 and the gaseous sulfur trioxide is fed into the second reaction step 43 via a line 53. The second reaction step thereby can be operated in liquid phase at such a temperature that the sulfur trioxide directly evaporates from the reaction mixture. Alternatively, the second reaction step 47 may comprise a reactor and an evaporation apparatus. In this case the alkanesulfonic acid and the sulfur trioxide are formed in the reactor and the reaction mixture is fed into the evaporation apparatus to separate the alkanesulfonic acid and the sulfur trioxide.

The invention claimed is:

1. A process for purifying alkanesulfonic anhydride, comprising:
   (a) feeding a stream comprising alkanesulfonic anhydride, sulfuric acid, high boilers and residual low boilers into a melt crystallization to form crystals of the alkanesulfonic anhydride suspended in mother liquor;
   (b) performing a solid-liquid separation to remove the crystals from the mother liquor and
   (c) optionally washing the crystals to remove mother liquor adhering to the crystals.

2. The process according to claim 1, wherein before feeding the stream comprising alkanesulfonic anhydride, sulfuric acid, high boilers and residual low boilers into the melt crystallization, a distillation for removing low boilers is carried out.

3. The process according to claim 2, wherein a crude product stream is fed into a distillation apparatus, the crude product stream comprising alkanesulfonic anhydride, sulfuric acid, high boilers and low boilers.

4. The process according to claim 1, wherein the mother liquor after removal of the crystals in (b) and/or the mother liquor generated in (a) is at least partly recycled into the melt crystallization.

5. The process according to claim 1, wherein the low boilers comprise sulfur trioxide.

6. The process according to claim 1, wherein the melt crystallization is carded out at a temperature in the range from 0 to 70° C.

7. The process according to claim 1, wherein step (c) is carried out and the crystals are washed with molten crystals of the pure alkanesulfonic anhydride.

8. The process according to claim 7, wherein the molten crystallizate for washing the crystals has a temperature 0.1° C. to 15° C. above the solidification temperature of the alkanesulfonic-anhydride-containing crystallizate.

9. The process according to claim 1, wherein the alkanesulfonic anhydride is methanesulfonic anhydride.

10. A process for producing and purifying alkanesulfonic anhydride comprising:
    (i) optionally distilling a melt comprising crude alkanesulfonic acid to completely or partly remove low boilers obtaining a material stream comprising alkanesulfonic acid, high boilers and residual low boilers;
    (ii) feeding the material stream comprising alkanesulfonic acid, high boilers and residual low boilers as a first stream and sulfur trioxide as a second stream into a reaction stage where the alkanesulfonic acid reacts with the sulfur trioxide forming alkanesulfonic anhydride; and
    (iii) purifying the alkanesulfonic anhydride in a process comprising
       (a) feeding a stream comprising alkanesulfonic anhydride, sulfuric acid, high boilers and residual low boilers into a melt crystallization to form crystals of the alkanesulfonic anhydride suspended in mother liquor;
       (b) performing a solid-liquid separation to remove the crystals from the mother liquor.

11. The process according to claim 10, wherein the low boilers comprise sulfur trioxide.

12. A process for producing anhydrous alkanesulfonic acid, comprising:
    purifying alkanesulfonic anhydride by a process comprising feeding a stream comprising alkanesulfonic anhydride, sulfuric acid, high boilers and residual low boilers into a melt crystallization to form crystals of the alkanesulfonic anhydride suspended in mother liquor; and performing a solid-liquid separation to remove the crystals from the mother liquor; and
    solving the crystals in a water-containing alkanesulfonic acid, wherein the water of the water-containing alkanesulfonic acid reacts with the alkanesulfonic anhydride forming alkanesulfonic acid or mixing equimolar amounts of the alkanesulfonic anhydride and water wherein the water reacts with the alkanesulfonic anhydride forming alkanesulfonic acid.

13. The process according to claim 12, wherein the water-containing alkanesulfonic acid is alkanesulfonic acid hydrate.

14. A process for producing peroxoalkanesulfonic acid, comprising:
    purifying alkanesulfonic anhydride by a process comprising feeding a stream comprising alkanesulfonic anhydride, sulfuric acid, high boilers and residual low boilers into a melt crystallization to form crystals of the alkanesulfonic anhydride, suspended in mother liquor; and performing a solid-liquid separation to remove the crystals from the mother liquor; and
    adding the purified alkanesulfonic anhydride to a mixture comprising water and hydrogen peroxide, wherein the hydrogen peroxide reacts with the alkanesulfonic anhydride forming peroxoalkanesulfonic acid and the water reacts with the alkanesulfonic anhydride forming alkanesulfonic acid.

15. A process for producing alkanesulfonic acid, comprising:
    purifying alkanesulfonic anhydride by a process comprising feeding a stream comprising alkanesulfonic anhydride, sulfuric acid, high boilers and residual low boilers into a melt crystallization to form crystals of the alkanesulfonic anhydride suspended in mother liquor; and performing a solid-liquid separation to remove the crystals from the mother liquor; and
    adding the purified alkanesulfonic acid to a mixture comprising sulfuric acid, wherein the sulfuric acid reacts with the alkanesulfonic anhydride forming alkanesulfonic acid and sulfur trioxide.

16. The process according to claim 15, wherein the sulfur trioxide is recycled into a process for producing crude alkanesulfonic acid or into a process for producing alkanesulfonic anhydride.

17. The process according to claim 15, wherein the alkanesulfonic acid is methanesulfonic acid.

18. The process according to claim 14, wherein the peroxoalkanesulfonic acid is added as an initiator to sulphur trioxide and alkane to start a radical chain reaction for producing alkanesulfonic acid or alkanesulfonic anhydride.

19. The process according to claim 12, wherein the alkanesulfonic acid is methanesulfonic acid.

20. The process according to claim 14, wherein the alkanesulfonic acid is methanesulfonic acid.

\* \* \* \* \*

UNITED STATES PATENT AND TRADEMARK OFFICE
CERTIFICATE OF CORRECTION

PATENT NO. : 10,730,827 B2
APPLICATION NO. : 16/605973
DATED : August 4, 2020
INVENTOR(S) : Juergen Wortmann et al.

It is certified that error appears in the above-identified patent and that said Letters Patent is hereby corrected as shown below:

On the Title Page

In Column 2, item (56), Other Publications, Line 19, "Socety," should read -- Society, --;

In Column 2, item (56), Other Publications, Lines 20-21, "Quelques proprietes physico-chlmiques des acides ethane- et methane-sulfonlque" and insert -- Quelques proprietes physico-chimiques des acides ethane- et methane-sulfonique --;

In Column 2, item (56), Other Publications, Line 23, "Methnesulphonic" should read -- Methanesulfonic --.

In the Specification

In Column 4, Line 63, "ON" should read -- CN --.

In Column 5, Line 52, "Chalogenated" should read -- C-halogenated --.

In Column 6, Line 16, "(i)" should read -- (i). --;

In Column 6, Line 35, "A A" should be -- A --;

In Column 6, Line 61, "alkanesulfonicanhydride" should read -- alkanesulfonic anhydride --.

In Column 8, Line 16, "methanesulfonc" should read -- methanesulfonic --.

In Column 11, Line 56, delete "aquous" should read -- aqueous --.

In Column 12, Line 37, should read "watercomprising" should read -- water comprising --.

Signed and Sealed this
Nineteenth Day of January, 2021

Andrei Iancu
*Director of the United States Patent and Trademark Office*

CERTIFICATE OF CORRECTION (continued)
U.S. Pat. No. 10,730,827 B2

In the Claims

In Column 15, Line 41, Claim 6, should read "carded" should read -- carried --.

In Column 16, Line 34, Claim 14, "anhydride," should read -- anhydride --.